(12) United States Patent
Degli-Esposti Rankin et al.

(10) Patent No.: US 7,416,877 B1
(45) Date of Patent: Aug. 26, 2008

(54) RECEPTOR THAT CAUSES CELL DEATH AND RECOMBINANT PRODUCTION THEREOF

(75) Inventors: Mariapia A. Degli-Esposti Rankin, Seattle, WA (US); Raymond G. Goodwin, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 08/943,776

(22) Filed: Oct. 3, 1997

Related U.S. Application Data

(60) Provisional application No. 60/044,456, filed on Oct. 4, 1996.

(51) Int. Cl.
*C07K 14/47* (2006.01)
*C07K 14/705* (2006.01)
(52) U.S. Cl. .................. 435/252.3; 435/69.1; 435/69.7; 536/23.5; 536/23.4; 530/350
(58) Field of Classification Search ................ 435/69.1, 435/320.1, 325; 526/23.5; 530/350
See application file for complete search history.

(56) References Cited

U.S. PATENT DOCUMENTS

| | | | | |
|---|---|---|---|---|
| 5,674,996 | A | * 10/1997 | Hartwell et al. | 536/24.31 |
| 6,153,402 | A | * 11/2000 | Yu | 435/69.1 |
| 6,462,176 | B1 | 10/2002 | Ashkenazi | |

2002/0192729 A1 12/2002 Ashkenazi

OTHER PUBLICATIONS

Screaton et al., Proc Natl Acad.Sci USA 94(9):4615-19, Apr. 1997.*
Marsters et al., Curr.Biol., 6(12): 1669-76, Dec. 1996.*
Chinnayian et al., Science 27495289):990-2, Nov. 1996.*
Wiley et al., Immunity 3(6):673-82, Dec. 1995.*
EST fragment H46211, Jul. 1995.*
EST fragment H46374, Jul. 1995.*
Bodmer et al., Immunity 6(1):79-88, 1997.*
Callard et al, The Cytokine FactsBook, Academic Press Ltd, p. 31 ), 1994.*
George et al., Macromolecular sequencing and synthesis, Alan Riss , p. 127-149, 1988.*
Maniatis et al., Molecular Cloning, A laboratory manual, Cold Spring Harbor Laboratory, vol. II, pp. 324-325, 1982.*
EST NCBI accession No. H41522, 1995.
EST NCBI accession No. H46374, 1995.
EST NCBI accession No. H46211, 1995.
EST NCBI accession No. H46662, 1995.
EST NCBI accession No. H46424, 1995.
Chinnaiyan et al., *Science* 274:990, 1996.
Kitson et al., *Nature* 384:372, 1996.
Marsters et al., *Current Biology* 6:1669, 1996.

* cited by examiner

*Primary Examiner*—Lorraine Spector
(74) *Attorney, Agent, or Firm*—Patricia Anne Perkins; Christine M. Bellas

(57) ABSTRACT

Isolated apoptosis inducing receptors, DNAs encoding such receptors, and pharmaceutical compositions made therefrom, are disclosed. The isolated receptors can be used to regulate an immune response. The receptors are also useful in screening for inhibitors thereof.

12 Claims, 1 Drawing Sheet

```
AIR:   LYDVMDAVPARRWKEFVRTLGLREAEIEAVEVEIGRF-RDQQYEMLKRWRQQP---AGLGAVYAALERMGLDGCVEDLRSRL
       LY V++ VP  RWKEFVR LGL + EI+ +E++ GR  R+ QY ML  WR++ P   A L  +   L  M L GC+ED+   L
INFRI: LYAVVENVPPLRWKEFVRRLGLSDHEIDRLELQNGRCLREAQYSMLATWRRTPRREATLELLGRVLRDMDLLGCLEDIEEAL
```

FIGURE 1

RECEPTOR THAT CAUSES CELL DEATH AND RECOMBINANT PRODUCTION THEREOF

CROSS-REFERENCE TO RELATED APPLICATION

This application claims the benefit of U.S. provisional application Ser. No. 60/044,456, filed Oct. 4, 1996, the entire disclosure of which is relied upon and incorporated by reference herein.

TECHNICAL FIELD OF THE INVENTION

The present invention relates generally to the field of cytokine receptors, and more specifically to cytokine receptor proteins having immunoregulatory activity.

BACKGROUND OF THE INVENTION

Efficient functioning of the immune system requires a fine balance between cell proliferation and differentiation and cell death, to ensure that the immune system is capable of reacting to foreign, but not self antigens. Central tolerance refers to the mechanisms which lead to positive and negative selection of T cells in the thymus where T cells are positively or negatively selected depending on their capacity to interact with self MHC antigens expressed in the thymus. In the periphery, mature T cells which interact with self antigens expressed uniquely in the periphery are deleted, as are T cells which have been activated by foreign antigen. This is known as peripheral tolerance.

Deletion of inappropriately activated T cells is believed to occur via programmed cell death known as apoptosis, which is distinct from cell death due to necrosis. Two members of the TNF family, Fas ligand (FasL) and TNF, have been reported to be involved in some of the effector mechanisms which control immune tolerance (reviewed in Cleveland and Ihle, *Cell* 81:479; 1995). FasL and TNF mediate their biological effects by binding their respective receptors, which are members of the TNFR superfamily (Smith et al., *Cell* 76:959; 1994).

Fas (the receptor for FasL) and TNF receptor type I (TNFRI) both contain a unique motif within their cytoplasmic regions, which has been termed the death domain (Tartaglia et al., *Cell* 74:845, 1993; Itoh and Nagata, *J. Biol. Chem.* 268:10932, 1993). Overexpression of the death domain in transient transfection systems has been shown to result in apoptosis. The biological effects of Fas/FasL and TNF/TNFRI interactions are thought to occur through both distinct and similar signaling pathways (Schultze-Osthoff et al., *EMBO J.* 13:4587, 1994; Wong and Goeddel, *J. Immunol.* 152:1751, 1994).

The lpr and gld mouse models have implicated the Fas/FasL system in peripheral tolerance; however, peripheral T cell deletion does occur in lpr mice. This Fas-independent apoptosis of mature T cells has been shown to be partly TNF mediated (Zheng et al., *Nature* 377:348, 1995) These data imply that multiple apoptotic mechanisms, including unrecognized ones, may be involved in peripheral tolerance. Moreover, the mechanisms mediating central tolerance remain unknown. Investigation into the existence and identity of other molecule(s) that play a role in apoptosis is desirable. Identifying such molecules would provide an additional means of regulating apoptosis, as well as providing further insight into the development of self-tolerance by the immune system and the etiology of autoimmune diseases.

SUMMARY OF THE INVENTION

The present invention identifies a novel receptor, referred to as Apoptosis Inducing Receptor (AIR) that induces apoptosis of certain cells on which it is expressed. The receptor is a Type I transmembrane protein having 417 amino acid residues. Soluble forms of the receptor can be prepared and used to regulate cell death in a therapeutic setting; accordingly, pharmaceutical compositions comprising soluble forms of the novel receptor are also provided. Soluble forms of the receptor will also be useful in vitro to block apoptosis of AIR-expressing cells, or to screen for agonists or antagonists of AIR activity. The cytoplasmic domain of AIR will be useful in developing assays for inhibitors of AIR-induced cell death. Such inhibitors will have use in regulating cell death in a therapeutic setting as well as in vitro. Deleted forms and fusion proteins comprising the novel receptor are also disclosed. Agonists of AIR activity can be used to kill tumor cells that express AIR, or kill T cells expressing AIR in autoimmune diseases. These and other aspects of the present invention will become evident upon reference to the following detailed description of the invention.

BRIEF DESCRIPTION OF THE DRAWINGS

FIG. 1 presents an alignment of AIR and TNFRI death domain sequences. The 83 amino acid sequence of the TNFRI death domain is compared to the homologous sequence from the AIR cytoplasmic region. Identical and conserved amino acids (+) are shown in the middle line.

DETAILED DESCRIPTION OF THE INVENTION

A new TNF receptor-like sequence was identified in the EST database. Oligonucleotide primers were synthesized based on the EST sequence, and a full-length cDNA was cloned from a peripheral blood T cell library. The encoded protein was designated AIR, for Apoptosis Inducing Receptor. The receptor is a Type I transmembrane protein having 417 amino acid residues, with a predicted 24 amino acid signal sequence, a 173 amino acid extracellular domain, a 27 amino acid transmembrane domain, and a 193 amino acid cytoplasmic tail. The cytoplasmic region of AIR displayed significant amino acid homology (48% identity, 64% similarity) to the 83 amino acid sequence which encodes the Type I TNF receptor death domain. This region, conserved between TNFRI and Fas, is necessary and sufficient for transduction of an apoptotic signal to a cell expressing AIR.

A search of the NCBI databank identified five expressed sequence tags (ESTs) having regions of identity with AIR DNA. These ESTs (NCBI accession numbers H41522, H46374, H46211, H46662, and H46424) are all human cDNA fragments. The NCBI records do not disclose any polypeptide encoded by the ESTs, and do not indicate what the reading frame, if any, might be. However, even if the knowledge of the reading frame revealed herein by disclosure of complete AIR coding regions is used to express the ESTs, none of the encoded polypeptides would have the biological properties of the presently-claimed AIR polypeptides. In other words, if each of the five ESTs were inserted into expression vectors downstream from an initiator methionine codon, in the reading frame elucidated herein, none of the resulting expressed polypeptides would contain a sufficient portion of the AIR protein to induce apoptosis.

Apoptosis and the TNF/TNFR Superfamilies

Efficient functioning of the immune system requires a fine balance between cell proliferation and differentiation and cell death. Central tolerance refers to the mechanisms which lead to positive and negative selection of T cells in the thymus. It is believed that T cells are positively or negatively selected depending on their capacity to interact with self MHC antigens expressed in the thymus: autoreactive T cells are eliminated, while those that recognize non-self antigens are selected for survival and differentiation. In the periphery, mature T cells which interact with self antigens expressed uniquely in the periphery are deleted, as are T cells which have been activated by foreign antigen. These mechanisms ensure that the immune system is capable of reacting to foreign, but not self antigens and that activated lymphocytes are removed after they have fulfilled their role Two members of the TNFR superfamily, Fas and TNFRI, are believed to play an important role in some of the effector mechanisms which control peripheral tolerance. Fas has been reported to mediate apoptosis and is believed to play a role in clonal deletion of self-reactive T-cells (Itoh et al., *Cell* 66:233, 1991; Watanabe-Fukunage et al., *Nature* 356:314, 1992). DNAs encoding Fas ligand have been isolated; binding of the Fas ligand to cells expressing Fas antigen has been demonstrated to induce apoptosis (Suda et al., *Cell,* 75:1169, 1993; Takahashi et al., *International Immunology* 6:1567, 1994). The lpr and gld mouse models have implicated the Fas/FasL system in the processes which lead to elimination of T cells after they have been activated by self or foreign antigen in the periphery. However, some peripheral T cell deletion still occurs in lpr mice. This Fas-independent apoptosis of mature T cells has been shown to be partly TNF mediated.

Elimination of these T cells occurs by apoptosis, a morphologically defined type of cell death that can be differentiated from necrosis. Fas and TNFRI both contain a death domain, a unique motif present within their cytoplasmic regions (Tartaglia et al., *Cell* 74:845, 1993; Itoh and Nagata, *J. Biol. Chem.* 268:10932, 1993). This domain shows some similarity with a Drosophila protein referred to as reaper which is required for most, if not all programmed cell death in this species (White et al., *Science* 264:677, 1994). Overexpression of the death domain in transient transfection systems has been shown to result in apoptosis.

The biological effects of Fas/FasL and TNF/TNFRI interactions are thought to occur through both distinct and similar signaling pathways (Schultze-Osthoff et al., *EMBO J.* 13:4587, 1994; Wong and Goeddel, *J. Immunol.* 152:1751, 1994). Both receptors couple ligand binding to tyrosine phosphorylation, and both activate sphingomyelinases. Cysteine proteinases have also been implicated in both FasL- and TNF-induced cell death; crmA, a product of the cowpox virus that inhibits cysteine proteases, inhibits both FasL- and TNF-induced apoptosis. Both FasL and TNF induce cell death within a few hours of binding their respective receptors, indicating that both signal pathways modulate latent cytoplasmic effector molecules; however, death induced by TNF tends to be slower than that induced by FasL.

The body of data currently available regarding apoptosis imply that multiple apoptotic mechanisms, including those mediated by Fas and TNFRI as well as additional, unrecognized ligand/receptor interactions, may be involved in peripheral tolerance within the immune system. In addition, the mechanism or mechanisms mediating central tolerance remain unknown. FasL and TNF are unlikely to be involved in the latter, since positive and negative selection in the thymus appear normal in lpr and TNFR knock-out mice. The novel receptor described herein shares certain similarities with both Fas and TNFRI, and could be important in regulating cell death during the development of self-tolerance (either in the periphery or the thymus).

DNAs, Proteins and Analogs

The present invention provides isolated AIR polypeptides and analogs (or muteins) thereof having an AIR activity (i.e., causing apoptosis of cells expressing an AIR mutein or analog comprising the death domain when triggered appropriately; or for soluble forms, binding to AIR-specific antibodies or inhibition of apoptosis induced by signalling through AIR). Such proteins are substantially free of contaminating endogenous materials and, optionally, without associated native-pattern glycosylation. Derivatives of AIR within the scope of the invention also include various structural forms of the primary protein which retain biological activity. Due to the presence of ionizable amino and carboxyl groups, for example, an AIR protein may be in the form of acidic or basic salts, or may be in neutral form. Individual amino acid residues may also be modified by oxidation or reduction. The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini.

Derivatives of AIR may also be obtained by cross-linking agents, such as M-maleimidobenzoyl succinimide ester and N-hydroxysuccinimide, at cysteine and lysine residues. The inventive proteins may also be covalently bound through reactive side groups to various insoluble substrates, such as cyanogen bromide-activated, bisoxirane-activated, carbonyl-diimidazole-activated or tosyl-activated agarose structures, or by adsorbing to polyolefin surfaces (with or without glutaraldehyde cross-linking). Once bound to a substrate, proteins may be used to selectively bind (for purposes of assay or purification) antibodies raised against the AIR or against other proteins which are similar to the AIR, as well as other proteins that bind AIR or its homologous proteins.

Soluble forms of AIR are also within the scope of the invention. The nucleotide and predicted amino acid sequence of the AIR is shown in SEQ ID NOs:1 and 2. Computer analysis indicated that the protein has an N-terminal signal peptide with a cleavage site between amino acid 24 and 25. Those skilled in the art will recognize that the actual cleavage site may be different than that predicted by computer analysis. Thus, the N-terminal amino acid of the cleaved peptide is expected to be within about five amino acids on either side of the predicted cleavage site. The signal peptide is predicted to be followed by a 173 amino acid extracellular domain, a 27 amino acid transmembrane domain, and a 193 amino acid cytoplasmic tail.

Soluble AIR comprises the signal peptide and the extracellular domain (residues 1 to 197 of SEQ ID NO:1) or a fragment thereof. Alternatively, a different signal peptide can be substituted for residues 1 through 24 of SEQ ID NO:1. Moreover, fragments of the extracellular domain will also provide soluble forms of AIR. Fragments can be prepared using known techniques to isolate a desired portion of the extracellular region, and can be prepared, for example, by comparing the extracellular region with those of other members of the TNFR family and selecting forms similar to those prepared for other family members. Alternatively, unique restriction sites or PCR techniques that are known in the art can be used to prepare numerous truncated forms which can be expressed and analyzed for activity.

Other derivatives of the AIR protein within the scope of this invention include covalent or aggregative conjugates of the protein or its fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader).

Protein fusions can comprise peptides added to facilitate purification or identification of AIR proteins and homologs (e.g., poly-His). The amino acid sequence of the inventive proteins can also be linked to an identification peptide such as that described by Hopp et al., *Bio/Technology* 6:1204 (1988). Such a highly antigenic peptide provides an epitope reversibly bound by a specific monoclonal antibody, enabling rapid assay and facile purification of expressed recombinant protein. The sequence of Hopp et al. is also specifically cleaved by bovine mucosal enterokinase, allowing removal of the peptide from the purified protein. Fusion proteins capped with such peptides may also be resistant to intracellular degradation in *E. coli*.

Fusion proteins further comprise the amino acid sequence of an AIR linked to an immunoglobulin Fc region. An exemplary Fc region is a human $IgG_1$ having a nucleotide and amino acid sequence set forth in SEQ ID NO:4. Fragments of an Fc region may also be used, as can Fc muteins. For example, certain residues within the hinge region of an Fc region are critical for high affinity binding to FcγRI. Canfield and Morrison (*J. Exp. Med.* 173:1483; 1991) reported that $Leu_{(234)}$ and $Leu_{(235)}$ were critical to high affinity binding of $IgG_3$ to FcγRI present on U937 cells. Similar results were obtained by Lund et al. (*J. Immunol.* 147:2657, 1991; *Molecular Immunol.* 29:53, 1991). Such mutations, alone or in combination, can be made in an $IgG_1$ Fc region to decrease the affinity of $IgG_1$ for FcR. Depending on the portion of the Fc region used, a fusion protein may be expressed as a dimer, through formation of interchain disulfide bonds. If the fusion proteins are made with both heavy and light chains of an antibody, it is possible to form a protein oligomer with as many as four AIR regions.

In another embodiment, AIR protein further comprises an oligomerizing zipper domain. Zipper domains are described in U.S. Ser. No. 08/107,353, filed Aug. 13, 1993, the relevant disclosure of which is incorporated by reference herein. Examples of leucine zipper domains are those found in the yeast transcription factor GCN4 and a heat-stable DNA-binding protein found in rat liver (C/EBP; Landschulz et al., *Science* 243:1681, 1989), the nuclear transforming proteins, fos and jun, which preferentially form a heterodimer (O'Shea et al., *Science* 245:646, 1989; Turner and Tjian, *Science* 243:1689, 1989), and the gene product of the murine proto-oncogene, c-myc (Landschulz et al., *Science* 240:1759, 1988). The fusogenic proteins of several different viruses, including paramyxovirus, coronavirus, measles virus and many retroviruses, also possess leucine zipper domains (Buckland and Wild, *Nature* 338:547, 1989; Britton, *Nature* 353:394, 1991; Delwart and Mosialos, *AIDS Research and Human Retroviruses* 6:703, 1990). Conservative amino acids may be substituted for individual leucine residues in dimer-forming zipper domains, with minimal decrease in the ability to dimerize.

Also included within the scope of the invention are fragments or derivatives of the intracellular domain of AIR. Such fragments are prepared by any of the herein-mentioned techniques, and include peptides that are identical to the cytoplasmic domain of AIR as shown in SEQ ID NO:1, and those that comprise a portion of the cytoplasmic region, for example, the death domain. All techniques used in preparing soluble forms may also be used in preparing fragments or analogs of the cytoplasmic domain (i.e., RT-PCR techniques or use of selected restriction enzymes to prepare truncations).

The present invention also includes AIR with or without associated native-pattern glycosylation. Proteins expressed in yeast or mammalian expression systems, e.g., COS-7 cells, may be similar or slightly different in molecular weight and glycosylation pattern than the native molecules, depending upon the expression system. Expression of DNAs encoding the inventive proteins in bacteria such as *E. coli* provides non-glycosylated molecules. Functional mutant analogs of AIR protein having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A_1$.

AIR protein derivatives may also be obtained by mutations of the native AIR or its subunits. An AIR mutated protein, as referred to herein, is a polypeptide homologous to an AIR protein but which has an amino acid sequence different from the native AIR because of one or a plurality of deletions, insertions or substitutions. The effect of any mutation made in a DNA encoding an AIR peptide may be easily determined by analyzing the ability of the mutated AIR peptide to inhibit AIR-induced cell death, for example, by AIR-specific antibodies. Moreover, activity of AIR analogs, muteins or derivatives can be determined by any of the assays described herein Analogs of the inventive proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present.

When a deletion or insertion strategy is adopted, the potential effect of the deletion or insertion on biological activity should be considered. Subunits of the inventive proteins may be constructed by deleting terminal or internal residues or sequences. Soluble forms of AIR can be readily prepared (for example, by using restriction enzymes to delete portions of the DNA encoding transmembrane and cytoplasmic regions) and tested for their ability to inhibit AIR-induced cell death. Polypeptides corresponding to the cytoplasmic regions, and fragments thereof (for example, the death domain) can be prepared by similar techniques. Additional guidance as to the types of mutations that can be made is provided by a comparison of the sequence of AIR to proteins that have similar structures, as well as by performing structural analysis of the inventive AIR proteins.

Generally, substitutions should be made conservatively; i.e., the most preferred substitute amino acids are those which do not affect the biological activity of AIR (i.e., ability of the inventive proteins to bind antibodies to AIR in a manner substantially equivalent to that of native AIR for muteins of the extracellular domain, or ability to induce apoptosis upon overexpression in transient transfection systems, for example). Examples of conservative substitutions include substitution of amino acids outside of the binding domain(s) (either ligand or antibody binding areas for the extracellular domain, or regions that interact with other, intracellular proteins for the cytoplasmic domain), and substitution of amino acids that do not alter the secondary and/or tertiary structure of native AIR. Additional examples include substituting one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

Mutations in nucleotide sequences constructed for expression of analog AIR or fragments thereof must, of course, preserve the reading frame phase of the coding sequences and preferably will not create complementary regions that could hybridize to produce secondary mRNA structures such as loops or hairpins which would adversely affect translation of the receptor mRNA.

Not all mutations in the nucleotide sequence which encodes an AIR protein or fragments thereof will be expressed in the final product, for example, nucleotide substitutions may be made to enhance expression, primarily to avoid secondary structure loops in the transcribed mRNA (see EPA 75,444A, incorporated herein by reference), or to provide codons that are more readily translated by the selected host, e.g., the well-known *E. coli* preference codons for *E. coli* expression.

Although a mutation site may be predetermined, it is not necessary that the nature of the mutation per se be predetermined. For example, in order to select for optimum characteristics of mutants, random mutagenesis may be conducted and the expressed mutated proteins screened for the desired activity. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, Jan. 1985, 12-19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

Other embodiments of the inventive proteins include AIR polypeptides encoded by DNAs capable of hybridizing under moderately stringent conditions (prewashing solution of 5×SSC, 0.5% SDS, 1.0 mM EDTA (pH 8.0) and hybridization conditions of 50° C., 5×SSC, overnight) to the DNA sequences encoding AIR, and other sequences which are degenerate to those which encode the AIR. In one embodiment, AIR polypeptides are at least about 70% identical in amino acid sequence to the amino acid sequence of native AIR protein as set forth in SEQ ID NO:1. In a preferred embodiment, AIR polypeptides are at least about 80% identical in amino acid sequence to the native form of AIR; most preferred polypeptides are those that are at least about 90% identical to native AIR.

Percent identity may be determined using a computer program, for example, the GAP computer program described by Devereux et al. (*Nucl. Acids Res.* 12:387, 1984) and available from the University of Wisconsin Genetics Computer Group (UWGCG). For fragments derived from the AIR protein, the identity is calculated based on that portion of the AIR protein that is present in the fragment The biological activity of AIR analogs of the extracellular domain can be determined by testing the ability of the analogs or muteins to inhibit AIR-induced cell death where death is triggered by an agonistic antibody or other agonist of AIR. Alternatively, suitable assays, for example, an enzyme immunoassay or a dot blot, employing an antibody that binds native AIR, can be used to assess the ability of AIR analogs or muteins to inhibit cell death. The biological activity of AIR analogs or muteins of the extracellular domain can be determined by testing the ability of the analogs to cause apoptosis when over-expressed in transfected cells. Alternatively, suitable assays, for example, signal transduction assays and methods that evaluate the ability of the cytoplasmic region of AIR to associate with other intracellular proteins involved in signal transduction will also be useful to asses the activity of AIR analogs or muteins. Such methods are well known in the art.

The invention also includes AIR DNAs, including any DNAs that encode the aforementioned AIR proteins and analogs. Due to code degeneracy, there can be considerable variation in nucleotide sequences encoding the same amino acid sequence. DNAs included within the embodiments of the invention are those capable of hybridizing under moderately stringent conditions (for example, prewashing solution of 5×SSC, 0.5% SDS, 1.0 mM EDTA (pH 8.0) and hybridization conditions of 50° C., 5×SSC, overnight), or, preferably, under stringent conditions (for example, hybridization in 6×SSC at 63° C. overnight; washing in 3×SSC at 55° C.), to the DNA of SEQ ID NO:1.

Fragments of the AIR nucleotide sequences are also useful. In one embodiment, such fragments comprise at least about 17 consecutive nucleotides, preferably at least about 25 nucleotides, more preferably at least 30 consecutive nucleotides, of the AIR DNA disclosed herein. DNA and RNA complements of such fragments are provided herein, along with both single-stranded and double-stranded forms of the AIR DNA of SEQ ID NO:1 or those encoding the aforementioned polypeptides. A fragment of AIR DNA generally comprises at least about 17 nucleotides, preferably from about 17 to about 30 nucleotides. Such nucleic acid fragments (for example, a probe corresponding to the extracellular domain of AIR) are use as a probe or as primers in a polymerase chain reaction (PCR).

The probes find use in detecting the presence of AIR nucleic acids in in vitro assays and in such procedures as Northern and Southern blots. Cell types expressing AIR can be identified as well. Such procedures are well known, and the skilled artisan can choose a probe of suitable length, depending on the particular intended application. For PCR, 5' and 3' primers corresponding to the termini of a desired AIR DNA sequence are employed to isolate and amplify that sequence, using conventional techniques.

Other useful fragments of the AIR nucleic acids are antisense or sense oligonucleotides comprising a single-stranded nucleic acid sequence (either RNA or DNA) capable of binding to target AIR mRNA (sense) or AIR DNA (antisense) sequences. The ability to create an antisense or a sense oligonucleotide, based upon a cDNA sequence for a given protein is described in, for example, Stein and Cohen, *Cancer Res.* 48:2659, 1988 and van der Krol et al., *BioTechniques* 6:958, 1988.

Uses of DNAs, Proteins and Analogs The AIR DNAs, proteins and analogs described herein will have numerous uses, including the preparation of pharmaceutical compositions. For example, soluble forms of AIR will be useful as antagonists of AIR-mediated apoptosis. AIR compositions (both protein and DNAs) will also be useful in development of both agonistic and antagonistic antibodies to AIR. The former will be useful in inducing cell death in, for example, tumor cells or auto-reactive T cells that express AIR; the latter will be useful in inhibiting apoptosis of AIR-expressing cells. The inventive DNAs are useful for the expression of recombinant proteins, and as probes for analysis (either quantitative or qualitative) of the presence or distribution of AIR transcripts. Antagonists of AIR will be useful in vitro to facilitate culture of cells (such as PBT) that express AIR.

The inventive proteins will also be useful in preparing kits that are used to detect soluble AIR or monitor AIR-related apoptotic activity, for example, in patient specimens. AIR proteins will also find uses in monitoring AIR-related apoptotic activity in other samples or compositions, as is necessary when screening for antagonists or mimetics of this activity (for example, peptides or small molecules that inhibit or mimic, respectively, the interaction). A variety of assay formats are useful in such kits, including (but not limited to) ELISA, dot blot, solid phase binding assays (such as those using a biosensor), rapid format assays and bioassays.

The purified AIR according to the invention will facilitate the discovery of inhibitors of AIR, and thus, inhibitors of AIR-induced cell death. The use of a purified AIR polypeptide in the screening for potential inhibitors is important and can virtually eliminate the possibility of interfering reactions with contaminants. Such a screening assay can utilize either the extracellular domain of AIR, the intracellular domain, or a fragment of either of these polypeptides. Detecting the AIR-induced apoptotic inhibiting activity of a molecule would typically involve use of a soluble form of AIR derived from the extracellular domain in a screening assay to detect molecules capable of binding AIR and inhibiting binding of, for example, an agonistic antibody, or using a polypeptide derived from the extracellular domain in an assay to detect inhibition of the interaction of AIR and other, intracellular proteins involved in signal transduction.

Moreover, in vitro systems can be used to ascertain the ability of molecules to antagonize or agonize AIR activity. Included in such methods are uses of AIR chimeras, for example, a chimera of the AIR intracellular domain and an extracellular domain derived from a protein having a known ligand. The effects on signal transduction of various molecule can then be monitored by utilizing the known ligand to transduce an apoptotic signal.

In addition, AIR polypeptides can also be used for structure-based design of AIR-inhibitors. Such structure-based design is also known as "rational drug design." The AIR polypeptides can be three-dimensionally analyzed by, for example, X-ray crystallography, nuclear magnetic resonance or homology modeling, all of which are well-known methods. The use of AIR structural information in molecular modeling software systems to assist in inhibitor design is also encompassed by the invention. Such computer-assisted modeling and drug design may utilize information such as chemical conformational analysis, electrostatic potential of the molecules, protein folding, etc. A particular method of the invention comprises analyzing the three dimensional structure of AIR for likely binding sites of substrates, synthesizing a new molecule that incorporates a predictive reactive site, and assaying the new molecule as described above.

Expression of Recombinant AIR

The proteins of the present invention are preferably produced by recombinant DNA methods by inserting a DNA sequence encoding AIR protein or a analog thereof into a recombinant expression vector and expressing the DNA sequence in a recombinant microbial expression system under conditions promoting expression. DNA sequences encoding the proteins provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors include synthetic or cDNA-derived DNA fragments encoding AIR, homologs, or bioequivalent analogs, operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. DNA sequences encoding AIR or homologs which are to be expressed in a microorganism will preferably contain no introns that could prematurely terminate transcription of DNA into mRNA.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage λ $P_L$ promoter and c1857ts thermolabile repressor. Plasmid vectors available from the American Type Culture Collection which incorporate derivatives of the λ $P_L$ promoter include plasmid pHUB2, resident in *E. coli* strain JMB9 (ATCC 37092) and pPLc28, resident in *E. coli* RR1 (ATCC 53082).

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al, (*Nature* 300:724, 1982). The yeast α-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included. Further, viral genomic promoter, control and/or signal sequences may be utilized, provided such control sequences are compatible with the host cell chosen. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986). A preferred eukaryotic vector for expression of AIR DNA is referred to as pDC406 (McMahan et al., *EMBO J.* 10:2821, 1991), and includes regulatory sequences derived from SV40, human immunodeficiency virus (HIV), and Epstein-Barr virus (EBV). Other preferred vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been deleted, making the Bgl II site within the multiple cloning site unique.

A useful cell line that allows for episomal replication of expression vectors, such as pDC406 and pDC409, which contain the EBV origin of replication, is CV-1/EBNA (ATCC CRL 10478). The CV-1/EBNA cell line was derived by transfection of the CV-1 cell line with a gene encoding Epstein-Barr virus nuclear antigen-1 (EBNA-1) and constitutively express EBNA-1 driven from human CMV immediate-early enhancer/promoter.

Host Cells

Transformed host cells are cells which have been transformed or transfected with expression vectors constructed using recombinant DNA techniques and which contain sequences encoding the proteins of the present invention. Transformed host cells may express the desired protein (AIR or homologs thereof), but host cells transformed for purposes of cloning or amplifying the inventive DNA do not need to express the protein. Expressed proteins will preferably be secreted into the culture supernatant, depending on the DNA selected, but may be deposited in the cell membrane.

Suitable host cells for expression of viral proteins include prokaryotes, yeast or higher eukaryotic cells under the control of appropriate promoters. Prokaryotes include gram negative or gram positive organisms, for example *E. coli* or *Bacillus* spp. Higher eukaryotic cells include established cell lines of mammalian origin as described below. Cell-free translation systems could also be employed to produce viral proteins using RNAs derived from the DNA constructs disclosed herein. Appropriate cloning and expression vectors for use with bacterial, fungal, yeast, and mammalian cellular hosts are described by Pouwels et al. (*Cloning Vectors: A Laboratory Manual*, Elsevier, New York, 1985), the relevant disclosure of which is hereby incorporated by reference.

Prokaryotic expression hosts may be used for expression of AIR or homologs that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera *Pseudomonas, Streptomyces*, and *Staphylococcus*, although others may also be employed as a matter of choice.

Recombinant AIR may also be expressed in yeast hosts, preferably from the *Saccharomyces* species, such as *S. cerevisiae*. Yeast of other genera, such as *Pichia* or *Kluyveromyces* may also be employed. Yeast vectors will generally contain an origin of replication from the 2µ yeast plasmid or an autonomously replicating sequence (ARS), promoter, DNA encoding the viral protein, sequences for polyadenylation and transcription termination and a selection gene. Preferably, yeast vectors will include an origin of replication and selectable marker permitting transformation of both yeast and *E. coli*, e.g., the amplicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable yeast transformation protocols are known to those of skill in the art; an exemplary technique is described by Hinnen et al., *Proc. Natl. Acad. Sci. USA* 75:1929, 1978, selecting for Trp$^+$ transformants in a selective medium consisting of 0.67% yeast nitrogen base, 0.5% casamino acids, 2% glucose, 10 µg/ml adenine and 20 µg/ml uracil. Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (*Cell* 23:175, 1981), and other cell lines capable of expressing an appropriate vector including, for example, CV-1/EBNA (ATCC CRL 10478), L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

Purification of Recombinant AIR

Purified AIR, homologs, or analogs are prepared by culturing suitable host/vector systems to express the recombinant translation products of the DNAs of the present invention, which are then purified from culture media or cell extracts. For example, supernatants from systems which secrete recombinant protein into culture media can be first concentrated using a commercially available protein concentration filter, for example, an Amicon or Millipore Pellicon ultrafiltration unit.

Following the concentration step, the concentrate can be applied to a suitable purification matrix. For example, a suitable affinity matrix can comprise a counter structure protein or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying the inventive proteins.

Affinity chromatography is a particularly preferred method of purifying AIR and homologs thereof. For example, an AIR expressed as a fusion protein comprising an immunoglobulin Fc region can be purified using Protein A or Protein G affinity chromatography. Moreover, an AIR protein comprising an oligomerizing zipper domain may be purified on a resin comprising an antibody specific to the oligomerizing zipper domain. Monoclonal antibodies against the AIR protein may also be useful in affinity chromatography purification, by utilizing methods that are well-known in the art. A ligand may also be used to prepare an affinity matrix for affinity purification of AIR.

Finally, one or more reversed-phase high performance liquid chromatography (RP-HPLC) steps employing hydrophobic RP-HPLC media, e.g., silica gel having pendant methyl or other aliphatic groups, can be employed to further purify an AIR composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant viral protein can be disrupted by any convenient method, including freeze-thaw cycling, sonication, mechanical disruption, or use of cell lysing agents.

Fermentation of yeast which express the inventive protein as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

Protein synthesized in recombinant culture is characterized by the presence of cell components, including proteins, in amounts and of a character which depend upon the purification steps taken to recover the inventive protein from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of the inventive proteins free of other proteins which may be normally associated with the proteins as they are found in nature in the species of origin.

Uses of Administration of AIR Compositions

The present invention provides methods of using therapeutic compositions comprising an effective amount of a protein and a suitable diluent and carrier, and methods for regulating an immune response. The use of AIR or homologs in conjunction with soluble cytokine receptors or cytokines, or other immunoregulatory molecules is also contemplated.

For therapeutic use, purified protein is administered to a patient, preferably a human, for treatment in a manner appropriate to the indication. Thus, for example, AIR protein compositions administered to regulate immune function can be given by bolus injection, continuous infusion, sustained release from implants, or other suitable technique. Typically, a therapeutic agent will be administered in the form of a composition comprising purified AIR, in conjunction with physiologically acceptable carriers, excipients or diluents. Such carriers will be nontoxic to recipients at the dosages and concentrations employed.

Ordinarily, the preparation of such protein compositions entails combining the inventive protein with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, on such factors as the nature and severity of the indication being treated, the desired response, the condition of the patient, and so forth.

Soluble forms of AIR and other AIR antagonists such as antagonistic monoclonal antibodies can be administered for the purpose of inhibiting AIR-induced cell death. AIR is expressed in activated T cells, and may play a in role in apoptotic death of these cells Soluble forms of AIR are thus likely to be useful in preventing or treating diseases in which T cells are inappropriately killed, for example, AIDS.

The following examples are offered by way of illustration, and not by way of limitation. Those skilled in the art will recognize that variations of the invention embodied in the examples can be made, especially in light of the teachings of the various references cited herein, the disclosures of which are incorporated by reference.

EXAMPLE 1

This example describes identification and isolation of a new tumor necrosis factor receptor-like protein. A cDNA having some degree of homology to Tumor Necrosis Factor receptor type I (TNFRI; p60, Schall, et al., *Cell*, 61:361, 1990); Loetscher, et al., *Cell*, 61:351, 1990), was identified in the NCBI EST (Expressed Sequence Tag) database (accession #H41522). Additional homologous ESTs were then identified (accession numbers H46374, H46424, H46211, H46662), and oligonucleotide primers were synthesized based on portions of the sequences that were conserved in the overlapping ESTs, had sequence of only about 50% GC, and contained no ambiguous nucleotides. The primers were used to determine the distribution of a potential corresponding RNA transcript in a variety of tissues using RT-PCR (reverse transcriptase-polymerase chain reaction) on a panel of first strand cDNAs substantially as described in U.S. Ser. No. 08/496,632, filed Jun. 29, 1995. Fetal brain was identified as a tissue in which mRNA corresponding to the identified sequence was transcribed; a human fetal brain cDNA library (Clontech, Palo Alto, Calif.) was screened using the PCR product described previously, which was labeled with $^{32}$P-dCTP by random priming or by additional PCR reaction. This process allowed the isolation of a number of cDNA clones which contained the sequences identified in the ESTs.

Sequence analysis confirmed the homology of the isolated cDNA to the TNF receptor family and showed conservation of the cysteine-rich pseudo-repeats which characterize the extracellular domain of members of this family. However, all the clones isolated lacked a leader peptide and a transmembrane region. Accordingly, additional clones were isolated form other libraries. Analysis of clones derived from a human peripheral blood T-cell (PBT) library (Park et al., *Blood* 74:56, 1989) allowed the isolation of a full length cDNA transcript, and also indicated that the clones obtained from fetal brain contained unspliced introns. After the full-length clone was isolated, it became clear that the ESTs contained nucleotide sequence derived from introns such as those present in the clones obtained from fetal brain.

The novel transcript isolated from the PBT library, referred to as apoptosis inducing receptor (AIR), encoded a 417 amino acids (aa) type I membrane protein with a 27 aa signal sequence, a 170 aa extracellular domain characterized by four cysteine-rich pseudo-repeats, a 27 aa transmembrane region and a 193 aa cytoplasmic region. The cytoplasmic region AIR contains a sequence that has the characteristics of a death domain, a region, conserved between TNFRI and Fas, which is necessary and sufficient for transduction of an apoptotic signal when signaling occurs via TNFRI or Fas (Tartaglia et al., *Cell* 74:845, 1993; Itoh and Nagata, *J. Biol. Chem.* 268: 10932, 1993). The death domain of AIR exhibits significant homology (48% identity, 64% similarity) to the 80 aa sequence which encodes the TNFRI death domain, and is also similar to the death domain of Fas (19.5% identity, 47% similarity). The nucleotide and amino acid sequence of AIR is shown in SEQ ID NO:1. The predicted signal peptide spans amino acids 1 through 24 of SEQ ID NO:1. Amino acids 198 through 224 are predicted to form a transmembrane region. Within the cytoplasmic region (amino acids 225 through 417), the putative death domain spans amino acids 335 through 413.

EXAMPLE 2

This example describes the cellular and tissue distribution of AIR mRNA. In order to determine the cellular and tissue distribution of AIR mRNA, poly (A)$^+$ RNA derived from various cell lines or tissues was examined by Northern blot analysis using the AIR cDNA as a probe. Filters containing poly(A)$^+$ RNA (2 µg per lane) from various tissues were purchased from Clontech (Palo Alto, Calif.). Polyadenylated RNA from various cells or cell lines were isolated, fractionated (2 µg per lane) on a 1% agarose formaldehyde gel, blotted onto Hybond nylon membrane (Amersham). Filters were probed with an anti-sense RNA riboprobe corresponding to the coding region of AIR cDNA. Hybridization was performed at 63° C. followed by three washings in 0.2%× SSC, 0.1% SDS at 68° C. Blots were exposed for 8 to 48 hr at −70° C.

Northern analysis showed strong expression of AIR in spleen, thymus and peripheral blood lymphocytes, with a predominant transcript ~3.0 kb together with a smaller ~1.5 kb transcript. Low level expression was observed in colon and small intestine. No transcripts were detected in ovary, testis, and prostate. The K299 cell line (established from peripheral blood of a patient diagnosed with high grade large cell anaplastic lymphoma) and the T cell line termed clone 22 also express AIR. Expression of AIR was also observed by RT-PCR in dendritic cells. Expression of the receptor can be regulated: PMA plus ionomycin stimulation of fresh PBTs leads to up-regulation of AIR message, whereas treatment of K299 cells with PMA plus ionomycin down-regulates AIR expression.

Chromosomal localization of AIR using a panel of radiation hybrids maps the gene to the telomeric end of human chromosome 1p, in close proximity to the region which encodes the genes for TNFRII, CD30 and OX40.

EXAMPLE 3

This example describes construction of a construct to express a soluble AIR/Flag® protein referred to as AIR/Flag. AIR/Flag® contains a leader sequence, and the region of AIR from amino acid 25 to amino acid 197 (SEQ ID NO:1), and the octapeptide referred to as Flag® (SEQ ID NO:3). The construct is prepared essentially as described for other soluble constructs, by ligating a DNA fragment encoding amino acids 25 through 197 of SEQ ID NO:1 (obtained by PCR or another suitable method) into an appropriate expression vector which contains a suitable leader sequence. The resultant DNA construct is transfected into a suitable cell line such as the monkey kidney cell line CV-1/EBNA (ATCC CRL 10478). AIR/Flag® may be purified using a Flag® antibody affinity column, and analyzed for biological activity using any of the methods described herein.

EXAMPLE 4

This example describes construction of an AIR DNA construct to express an AIR/Fc fusion protein. A soluble form of AIR fused to the Fc region of human IgG1 was constructed in the mammalian expression vector pDC409 (U.S. Ser. No.

08/571,579). This expression vector encompasses the leader sequence of the Cytomegalovirus open reading frame R27080, followed by amino acids 25-199 of AIR, followed by a mutated form of the constant domain of human IgG$_1$ (SEQ ID NO:4).

The AIR/Fc expression plasmid was transfected into CV-1/EBNA cells, and supernatants were collected for one week. The AIR/Fc fusion protein was purified on a protein A sepharose column (Pharmacia, Uppsala, Sweden) substantially as described in Example 5. Protein concentration was determined by an enzyme-linked immunoadsorbent assay specific for the constant domain of human IgG1 and by BCA analysis (Pharmacia), and purity was confirmed by SDS-polyacrylamide gel electrophoresis analysis followed by silver stain of the gel. SDS-PAGE (in the presence of a reducing agent) analysis of the purified AIR-Fc showed the protein migrated with a molecular weight of ~52 kDa. Interestingly, disulfide linked homodimers were found to only represent ~30% of the material, with higher order aggregates representing the remaining 70%.

EXAMPLE 5

This example describes purification of AIR fusion proteins. AIR/Fc fusion protein is purified by conventional methods using Protein A or Protein G chromatography. Approximately one liter of culture supernatant containing AIR/Fc fusion protein is purified by filtering mammalian cell supernatants (e.g., in a 0.45 m filter) and applying filtrate to a protein A/G antibody affinity column (Schleicher and Schuell, Keene, N.H.) at 4° C. at a flow rate of 80 ml/hr for a 1.5 cm×12.0 cm column. The column is washed with 0.5 M NaCl in PBS until free protein is not detected in the wash buffer. Finally, the column is washed with PBS. Bound fusion protein is eluted from the column with 25 mM citrate buffer, pH 2.8, and brought to pH 7 with 500 mM Hepes buffer, pH 9.1.

An AIR fusion protein comprising Flag® may also be detected and/or purified using an antibody that binds Flag®, substantially as described in Hopp et al., *Bio/Technology* 6:1204 (1988). Biological activity is measured by inhibition of AIR-induced cell death, for example, as described in the Examples herein.

EXAMPLE 6

This example illustrates the preparation of monoclonal antibodies against AIR. Preparations of purified recombinant AIR, for example, or transfected cells expressing high levels of AIR, are employed to generate monoclonal antibodies against AIR using conventional techniques, such as those disclosed in U.S. Pat. No. 4,411,993. DNA encoding AIR can also be used as an immunogen, for example, as reviewed by Pardoll and Beckerleg in *Immunity* 3:165, 1995. Such antibodies are likely to be useful in interfering with AIR-induced cell death (antagonistic antibodies) or in inducing apoptosis by cross-linking AIR (agonistic antibodies), as components of diagnostic or research assays for AIR or AIR activity, or in affinity purification of AIR.

To immunize rodents, AIR immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10-100 μg subcutaneously into a selected rodent, for example, BALB/c mice or Lewis rats. DNA may be given intradermally (Raz et al., *Proc. Natl. Acad. Sci. USA* 91:9519, 1994) or intamuscularly (Wang et al., *Proc. Natl. Acad. Sci. USA* 90:4156, 1993); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision for testing by dot-blot assay (antibody sandwich), ELISA (enzyme-linked immunosorbent assay), immunoprecipitation, or other suitable assays, including FACS analysis. Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with AIR, for example, by adaptations of the techniques disclosed by Engvall et al., *Immunochem.* 8:871 (1971) and in U.S. Pat. No. 4,703,004. A preferred screening technique is the antibody capture technique described by Beckman et al., *J. Immunol.* 144:4212 (1990). Positive clones are then injected into the peritoneal cavities of syngeneic rodents to produce ascites containing high concentrations (>1 mg/ml) of anti-AIR monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to AIR protein.

Monoclonal antibodies were generated using the AIR-Fc fusion protein as the immunogen. These reagents are screened to confirm reactivity against the AIR protein. Using the methods described herein to monitor the activity of the mAbs, both agonistic (i.e., antibodies that bind AIR and transduce an apoptotic signal) and antagonistic (i.e., antibodies that bind AIR and do not transduce an apoptotic signal, and in fact can inhibit apoptosis) are isolated.

EXAMPLE 7

This example illustrates the ability of AIR to cause apoptosis of transfected cells. To determine the apoptotic activity of AIR in the absence of a ligand, the full length transcript was over-expressed in a transient transfection system. This approach has been used successfully to demonstrate Fas and TNFRI mediated apoptosis and relies on the fact that self aggregation of death domain sequences induced by over-expression mimics the ligand mediated juxta-position of the cytoplasmic regions required for productive signaling.

CVI/EBNA cells (1.65×10$^5$ cells per slide) were transiently co-transfected a with total of 2 μg of DNA per slide, by the DEAE-dextran method. Each DNA mixture contained 0.5 μg of test transcript (pDC409-AIR; pDC302-TNFRI, or pDC302-FAS; pDC302 is described in Mosley et al., *Cell* 59:335, 1989), 0.25 μg of pDC409-β-glactosidase and 0.25 μg of pSV3neo plus 1.0 μg of pDC303-crmA (pDC303 is described in U.S. Pat. No. 5,350,683; crmA is a cowpox open reading frame which encodes an inhibitor of Interleukin-1β-converting enzyme that is capable of blocking apoptosis through Fas or TNFRI; see *Cell* 69:597, 1992) or 1.0 μg of empty pDC302 vector DNA. crmA, pDC302 and pDC409 controls were included in the experiment. All samples were supplemented with an appropriate amount of empty pDC302 vector DNA to keep the total amount of DNA per transfection constant. After 48 hours cells were washed with PBS, lysed with 1.0 ml of PBS+1% NP-40 for 30 min and the β-galactosidase activity determined using o-nitrophenyl-b-D-galactopyranoside as a substrate. The amount of β-galactosidase in the lysates (X-Gal u/ml) was determined by measuring the absorbance of the resulting colored product and comparing it to a known β-galactosidase standard. A decrease in the absorbance obtained in this assay indicates loss of β-galactosidase expression and correlates with death of cells that express the protein(s) co-transfected with β-galactosidase.

Over-expression of AIR in CVI/EBNA cells lead to cell death. Morphological and confocal microscope analyses suggested that the observed cell death was mediated by an apoptotic mechanism. Further evidence that AIR mediated apoptosis was obtained by Hoechst staining of the transfected cells. Like Fas-induced apoptosis, the AIR-mediated cell death was partially blocked by co-expression of crmA, the cowpox gene product which specifically inhibits the Interleukin-1β-converting enzyme. The cytoplasmic domain of AIR carrying the 80 aa death domain sequence is essential for transducing the apoptotic signal. This was demonstrated using a chimera containing the extracellular domain of CD40 fused to the transmembrane and cytoplasmic domains of AIR. Over-expression of the CD40-AIR chimera led to the same apoptosis observed when full length AIR was over-expressed.

EXAMPLE 7

This example demonstrates that a soluble AIR/Fc fusion protein can enhance the allostimulatory capacity of CD8α$^+$ dendritic cells (DC). CD8α$^+$ DC are a recently identified subset of antigen presenting cells which have been described as lymphoid-related DC (i.e. derived from a lymphoid committed BM progenitor which can give rise to T cells B cells and NK cells (Wu et al., *J. Exp. Med.* 184: 903, 1996). CD8α$^+$ DC express high levels of FasL and have been shown to kill activated, Fas expressing CD4$^+$ T cells in vitro (Süss and Shortman, *J. Exp. Med.* 183: 1789, 1996). In vitro studies have shown that CD8α$^+$ splenic DC are less efficient at stimulating the proliferation of allo-reactive and hemagglutinin-specific CD4$^+$ T cells (Süss and Shortman, supra).

Maraskovsky et al. (*J. Exp. Med.* 184:1953, 1996) found that the predominantly CD8α$^+$ lymphoid-related DC were 2-3-fold less efficient at stimulating the proliferation of allo-reactive or KLH-specific CD4$^+$ T cells as compared to other DC. Furthermore, the apparent deficit in T cell-stimulating capacity of CD8α$^+$ DC was actually due to their ability to directly induce the apoptotic death of the CD4$^+$ T cells during in vitro stimulation; this effect was obviated when using either DC from gld (FasL-/-) mice or CD4$^+$ T cells from lpr (Fas-/-) mice, implicating a direct role for FasL expressed on the CD8α$^+$ (Süss and Shortman, supra). This suggests that FasL expressing CD8α$^+$ DC can negatively regulate T cell activation via a programmed cell death pathway. However, the role of Fas-mediated killing has been shown to be only partially responsible for apoptosis of the target T cells, especially when the targets are CD8$^+$ T cells (Kronin et al, *J. Immunol.* 157: 3819, 1996).

In the case of CD8$^+$ T cells, the CD8α$^+$ DC were initially efficient at stimulating CD8$^+$ T cells to proliferate, but T cell proliferation was significantly reduced later in culture (Kronin et al, supra). Studies performed with lpr or gld mice indicated that Fas-induced apoptosis was not involved suggesting that the mechanism was distinct from that observed for CD4$^+$ T cells. The reduced proliferation was rescued only when high levels of IL-2 were added to the cultures, correlating with the significantly reduced IL-2 production observed for the CD8$^+$ T cells (IL-3, GM-CSF and IFN-γ production was also reduced, but IL-2 appeared to be the most limiting cytokine for the CD8$^+$ T cells). This indicated that CD8α$^+$ DC were actually not deficient in their ability to induce T cell proliferation but did not induce adequate cytokine production in the responding CD8$^+$ T cells. Thus, CD8$^+$ DC can kill activated CD4$^+$ T cells via a Fas-mediated pathway but also regulate CD8$^+$ T cell proliferation by controlling T cell cytokine production via an unknown pathway.

The regulatory nature of CD8α$^+$ DC is further demonstrated by Inaba, et al., *J. Exp. Med.* 186, 665 (1997), who show that the CD8α$^+$ DC which are localized in the T-cell areas of secondary lymphoid tissue, predominantly express MHC molecules occupied by self-peptides. Furthermore, these CD8α$^+$ DC induced the initial proliferation and then death of self-peptide reactive T cell clones in vitro. These findings indicate that CD8α$^+$ DC are functionally specialized to regulate the course of T cell activation and may play a critical role in the maintenance of peripheral tolerance to self-reactive T cells as well as regulate the development of the T cell cytokine repertoire.

Functionally mature CD8α$^+$ DC were isolated from the spleens of mice treated for nine consecutive days with CHO-derived human Flt3 ligand (FL) as previously reported (Maraskovsky et al., supra, and Pulendran et al., *J. Immunol.* 159:2222, 1997). FL has been shown to dramatically increase the numbers of DC in vivo (U.S. Ser. No. 08/539,142, filed Oct. 4, 1995). Briefly, spleen cells from FL-treated mice were incubated with the monoclonal antibodies (mAb), anti-B220 (for B cells), anti-Thy 1 (for T cells), anti-Gr-1 (for myeloid-cells), anti-NK 1.1 (for NK cells) and anti-Ter 119 (for erythroid cells) to label mature lineage cells.

The mAb coated cells were then incubated with magnetic beads coated with goat-anti-mouse and goat-anti-rat Ig (Dyna beads, Dynal Oslo, Norway). The subsequent mAb and magnetic bead coated cells (mature lineage cells) were removed from the cell suspension using a magnetic leaving behind an enriched population of DC. The depleted spleen cells were incubated with anti-CD11c (to identify DC) and anti-CD8α$^+$ to identify the CD8α$^+$ lymphoid-related DC. CD11c$^+$ CD8α$^+$ DC were then isolated at high purity (>95%) by fluorescence activated cell sorting (FACS) using a FACStar Plus™ (Becton Dickinson, San Jose, Calif.), and used for biological evaluation of AIR/Fc.

The mouse CD8α$^+$ DC expressed a counterstructure that bound the human AIR/Fc protein (prepared substantially as described in Example 4) at the cell surface, as assessed by flow cytometric analysis. Accordingly, the effect of AIR/Fc on the biological activity of the CD8α$^+$ DC was assessed. The addition of AIR/Fc to CD8α$^+$ DC enhanced their allostimulatory capacity in a mixed lymphocyte reaction (MLR). Allogeneic T cells (1×10$^5$) were incubated with varying numbers of irradiated (2000 rad) DC cultured as indicated above in 96-well round bottomed culture plates in 0.2 ml culture medium for four days. The cultures were pulsed with 0.5 mCi [$^3$H]-thymidine for eight hours and the cells harvested onto glass fiber sheets for counting on a gas phase β counter.

The potent apoptotic cell death induced by AIR suggests that in vivo the AIR/AIR ligand system may modulate cell death via the induction of apoptosis in a manner similar to that used by the Fas/FasL system. Given the high expression of AIR on T cells, and the of presence of an AIR counterstructure on the CD8α$^+$ DCs, it is possible that an interaction between AIR and the DC-expressed counterstructure may also contribute to the poor allostimulatory capacity of the CD8α$^+$ DC.

EXAMPLE 8

This example illustrates a cross-species hybridization technique which was used to isolate a murine AIR homolog using a probe designed from the sequence of human AIR. A human AIR probe was produced by $^{32}$P-labeling a 451 nucleotide fragment (327-778), encoding the extracellular domain of the human AIR protein, with random primers using the Primer It Kit (Stratagene, San Diego, Calif.). The murine 7B9 T cell (Mosley et al., *Cell* 59:335; 1989) derived cDNA library was constructed in a λ ZAP phage vector and packaged in vitro using a commercially available kit (Gigapak® Stratagene, San Diego, Calif.) according to the manufacturer's instructions, substantially as described in U.S. Pat. No. 5,599,905, issued Feb. 4, 1997).

The human AIR probe was hybridized to the cDNA library in a buffer containing 10×Denhardt's solution, 50 mM Tris pH 7.5, 1 M NaCl, 0.1% sodium pyrophosphate, 1×SDS and 200 mg/ml denatured salmon sperm DNA at 63° C. overnight. Hybridization was followed by washing 30 min in 6×SSC, 30 min in 2×SSC, 60 min in 1×SSC at 63° C. and 30 min in 0.5×SSC at room temperature. Hybridizing clones were visualized by autoradiography.

A clone was isolated carrying a sequence containing a complete coding region with homology to human AIR. This clone, however, also contained what appeared to be two intronic sequences. A fragment encoding the second and third cysteine-rich pseudo-repeats in the extracellular domain of the murine AIR cDNA clone was used to generate a single-stranded PCR probe which was used to re-screen the 7B9 cDNA library. The murine probe was hybridized to phage cDNA in Starks' buffer containing 50% formamide (Wahl et al, 1979, *PNAS* 76: 3683-3687) at 37° C. overnight. Hybridization was followed by 2×30 min washes in 2×SSC and 2×30 min washes in 0.5×SSC at 42° C. Hybridizing clones were visualized by autoradiography.

A clone was isolated containing a coding region identical to that of the previously isolated clone, but without intronic sequences. This clone, however, lacked the first 78 amino acids of murine AIR from the start methionine. A full length coding sequence cDNA construct was derived by PCR by joining the sequences from the two original cDNA clones without the introns. The nucleotide sequence and predicted amino acid sequence of this clone are illustrated SEQ ID NO:5 and 6. Similarly to human AIR, murine AIR is a Type I transmembrane protein having 411 amino acid residues, with a predicted 30 amino acid signal sequence, a 159 amino acid extracellular domain, a 21 amino acid transmembrane domain, and a 195 amino acid cytoplasmic tail. The cytoplasmic region of murine AIR displays significant amino acid homology to cytoplasmic region of human AIR and encodes a death domain motif.

---

We claim:

1. An isolated DNA molecule encoding a polypeptide comprising amino acids 1 through 411 of SEQ ID NO: 6, or a fragment thereof, wherein the fragment is capable of inducing apoptosis.

2. The DNA of claim 1 wherein the encoded fragment consists of amino acids 31 through 190 of SEQ ID NO: 6.

3. An isolated DNA molecule encoding a polypeptide comprising an amino acid sequence that is at least 70% identical to SEQ ID NO: 6, wherein the protein is capable of inducing apoptosis.

4. An isolated DNA molecule comprising SEQ ID NO: 5.

5. A recombinant expression vector comprising the DNA molecule of claim 1 or claim 4.

6. A host cell transformed or transfected with an expression vector according to claim 5.

7. A process for preparing a protein comprising amino acids 1 through 411 of SEQ ID NO: 6 or a fragment thereof, comprising culturing the host cell of claim 6 under conditions promoting expression of the protein.

8. An isolated polypeptide comprising the amino acid sequence set forth in SEQ ID NO: 6, or a fragment thereof, wherein the fragment is capable of inducing apoptosis.

9. The polypeptide of claim 8 wherein the polypeptide consists of amino acids 31 through 190 of SEQ ID NO: 6.

10. A fusion polypeptide comprising the polypeptide of claim 8.

11. An isolated polypeptide consisting of an amino acid sequence that is at least 70% identical to SEQ ID NO: 6, wherein the polypeptide is capable of inducing apoptosis.

12. An isolated polypeptide comprising the amino acid sequence set forth in SEQ ID NO: 6.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 1847 base pairs
        (B) TYPE: nucleic acid
        (C) STRANDEDNESS: single
        (D) TOPOLOGY: Not Relevant (ii) MOLECULE TYPE: cDNA (iii) HYPOTHETICAL: NO (iv) ANTI-SENSE: NO (vii) IMMEDIATE SOURCE:
        (B) CLONE: AIR (ix) FEATURE:
        (A) NAME/KEY: CDS
        (B) LOCATION: 236..1489

(xi) SEQUENCE DESCRIPTION: SEQ ID NO:1:

```
CTTTTCAGCC ATACCCGGAT GGTTCTGTCC TCGCTGGCCG TGATCACGCC GTCCTCCTTG        60

GGGATGAGCA GCGCGGCCGT GACGGCGTCC TGGTGCCCCT CGATCTTGCT CAGCAGCACC       120

GGGCGGCTGC TCTGCGGCCT GGAGTGGATT TCGGCCGCCA TGTTCGCGCG GCGACTGCTG       180

CGGCCTCCTC GGCAGGCAGC CCATCAGCTG ACGCCTGGGC GCCCGTCGGA GGGCT ATG        238
                                                             Met
                                                               1

GAG CAG CGG CCG CGG GGC TGC GCG GCG GTG GCG GCG GCG CTC CTC CTG        286
Glu Gln Arg Pro Arg Gly Cys Ala Ala Val Ala Ala Ala Leu Leu Leu
  5                  10                  15
```

-continued

```
GTG CTG CTG GGG GCC CGG GCC CAG GGC GGC ACT CGT AGC CCC AGG TGT      334
Val Leu Leu Gly Ala Arg Ala Gln Gly Gly Thr Arg Ser Pro Arg Cys
         20                  25                  30

GAC TGT GCC GGT GAC TTC CAC AAG AAG ATT GGT CTG TTT TGT TGC AGA      382
Asp Cys Ala Gly Asp Phe His Lys Lys Ile Gly Leu Phe Cys Cys Arg
     35                  40                  45

GGC TGC CCA GCG GGG CAC TAC CTG AAG GCC CCT GCC ACG GAG CCC TGC      430
Gly Cys Pro Ala Gly His Tyr Leu Lys Ala Pro Cys Thr Glu Pro Cys
 50                  55                  60                  65

GGC AAC TCC ACC TGC CTT GTG TGT CCC CAA GAC ACC TTC TTG GCC TGG      478
Gly Asn Ser Thr Cys Leu Val Cys Pro Gln Asp Thr Phe Leu Ala Trp
                 70                  75                  80

GAG AAC CAC CAT AAT TCT GAA TGT GCC CGC TGC CAG GCC TGT GAT GAG      526
Glu Asn His His Asn Ser Glu Cys Ala Arg Cys Gln Ala Cys Asp Glu
             85                  90                  95

CAG GCC TCC CAG GTG GCG CTG GAG AAC TGT TCA GCA GTG GCC GAC ACC      574
Gln Ala Ser Gln Val Ala Leu Glu Asn Cys Ser Ala Val Ala Asp Thr
        100                 105                 110

CGC TGT GGC TGT AAG CCA GGC TGG TTT GTG GAG TGC CAG GTC AGC CAA      622
Arg Cys Gly Cys Lys Pro Gly Trp Phe Val Glu Cys Gln Val Ser Gln
    115                 120                 125

TGT GTC AGC AGT TCA CCC TTC TAC TGC CAA CCA TGC CTA GAC TGC GGG      670
Cys Val Ser Ser Ser Pro Phe Tyr Cys Gln Pro Cys Leu Asp Cys Gly
130                 135                 140                 145

GCC CTG CAC CGC CAC ACA CGG CTA CTC TGT TCC CGC AGA GAT ACT GAC      718
Ala Leu His Arg His Thr Arg Leu Leu Cys Ser Arg Arg Asp Thr Asp
                150                 155                 160

TGT GGG ACC TGC CTG CCT GGC TTC TAT GAA CAT GGC GAT GGC TGC GTG      766
Cys Gly Thr Cys Leu Pro Gly Phe Tyr Glu His Gly Asp Gly Cys Val
            165                 170                 175

TCC TGC CCC ACG AGC ACC CTG GGG AGC TGT CCA GAG CGC TGT GCC GCT      814
Ser Cys Pro Thr Ser Thr Leu Gly Ser Cys Pro Glu Arg Cys Ala Ala
        180                 185                 190

GTC TGT GGC TGG AGG CAG ATG TTC TGG GTC CAG GTG CTC CTG GCT GGC      862
Val Cys Gly Trp Arg Gln Met Phe Trp Val Gln Val Leu Leu Ala Gly
    195                 200                 205

CTT GTG GTC CCC CTC CTG CTT GGG GCC ACC CTG ACC TAC ACA TAC CGC      910
Leu Val Val Pro Leu Leu Leu Gly Ala Thr Leu Thr Tyr Thr Tyr Arg
210                 215                 220                 225

CAC TGC TGG CCT CAC AAG CCC CTG GTT ACT GCA GAT GAA GCT GGG ATG      958
His Cys Trp Pro His Lys Pro Leu Val Thr Ala Asp Glu Ala Gly Met
                230                 235                 240

GAG GCT CTG ACC CCA CCA CCG GCC ACC CAT CTG TCA CCC TTG GAC AGC     1006
Glu Ala Leu Thr Pro Pro Pro Ala Thr His Leu Ser Pro Leu Asp Ser
            245                 250                 255

GCC CAC ACC CTT CTA GCA CCT CCT GAC AGC AGT GAG AAG ATC TGC ACC     1054
Ala His Thr Leu Leu Ala Pro Pro Asp Ser Ser Glu Lys Ile Cys Thr
        260                 265                 270

GTC CAG TTG GTG GGT AAC AGC TGG ACC CCT GGC TAC CCC GAG ACC CAG     1102
Val Gln Leu Val Gly Asn Ser Trp Thr Pro Gly Tyr Pro Glu Thr Gln
    275                 280                 285

GAG GCG CTC TGC CCG CAG GTG ACA TGG TCC TGG GAC CAG TTG CCC AGC     1150
Glu Ala Leu Cys Pro Gln Val Thr Trp Ser Trp Asp Gln Leu Pro Ser
290                 295                 300                 305

AGA GCT CTT GGC CCC GCT GCT GCG CCC ACA CTC TCG CCA GAG TCC CCA     1198
Arg Ala Leu Gly Pro Ala Ala Ala Pro Thr Leu Ser Pro Glu Ser Pro
                310                 315                 320

GCC GGC TCG CCA GCC ATG ATG CTG CAG CCG GGC CCG CAG CTC TAC GAC     1246
Ala Gly Ser Pro Ala Met Met Leu Gln Pro Gly Pro Gln Leu Tyr Asp
            325                 330                 335
```

-continued

```
GTG ATG GAC GCG GTC CCA GCG CGG CGC TGG AAG GAG TTC GTG CGC ACG         1294
Val Met Asp Ala Val Pro Ala Arg Arg Trp Lys Glu Phe Val Arg Thr
        340                 345                 350

CTG GGG CTG CGC GAG GCA GAG ATC GAA GCC GTG GAG GTG GAG ATC GGC         1342
Leu Gly Leu Arg Glu Ala Glu Ile Glu Ala Val Glu Val Glu Ile Gly
    355                 360                 365

CGC TTC CGA GAC CAG CAG TAC GAG ATG CTC AAG CGC TGG CGC CAG CAG         1390
Arg Phe Arg Asp Gln Gln Tyr Glu Met Leu Lys Arg Trp Arg Gln Gln
370                 375                 380                 385

CAG CCC GCG GGC CTC GGA GCC GTT TAC GCG GCC CTG GAG CGC ATG GGG         1438
Gln Pro Ala Gly Leu Gly Ala Val Tyr Ala Ala Leu Glu Arg Met Gly
                390                 395                 400

CTG GAC GGC TGC GTG GAA GAC TTG CGC AGC CGC CTG CAG CGC GGC CCG         1486
Leu Asp Gly Cys Val Glu Asp Leu Arg Ser Arg Leu Gln Arg Gly Pro
            405                 410                 415

TGA CACGGCGCCC ACTTGCCACC TAGGCGCTCT GGTGGCCCTT GCAGAAGCCC              1539
 *

TAAGTACGGT TACTTATGCG TGTAGACATT TTATGTCACT TATTAAGCCG CTGGCACGGC        1599

CCTGCGTAGC AGCACCAGCC GGCCCCACCC CTGCTCGCCC CTATCGCTCC AGCCAAGGCG        1659

AAGAAGCACG AACGAATGTC GAGAGGGGGT GAAGACATTT CTCAACTTCT CGGCCGGAGT        1719

TTGGCTGAGA TCGCGGTATT AAATCTGTGA AGAAAACAA AAAAAAAAAA ACCGGAATTC        1779

GATATCAAGC TTATCGATAC CGTCGACCTC GAGGGGGGGC CCGGTACCCA ATTCGCCCTA        1839

TAGTGAGT                                                                 1847

(2) INFORMATION FOR SEQ ID NO:2:

(i) SEQUENCE CHARACTERISTICS:
        (A) LENGTH: 417 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Gln Arg Pro Arg Gly Cys Ala Ala Val Ala Ala Ala Leu Leu
 1               5                  10                  15

Leu Val Leu Leu Gly Ala Arg Ala Gln Gly Gly Thr Arg Ser Pro Arg
            20                  25                  30

Cys Asp Cys Ala Gly Asp Phe His Lys Lys Ile Gly Leu Phe Cys Cys
        35                  40                  45

Arg Gly Cys Pro Ala Gly His Tyr Leu Lys Ala Pro Cys Thr Glu Pro
    50                  55                  60

Cys Gly Asn Ser Thr Cys Leu Val Cys Pro Gln Asp Thr Phe Leu Ala
65                  70                  75                  80

Trp Glu Asn His His Asn Ser Glu Cys Ala Arg Cys Gln Ala Cys Asp
                85                  90                  95

Glu Gln Ala Ser Gln Val Ala Leu Glu Asn Cys Ser Ala Val Ala Asp
            100                 105                 110

Thr Arg Cys Gly Cys Lys Pro Gly Trp Phe Val Glu Cys Gln Val Ser
        115                 120                 125

Gln Cys Val Ser Ser Ser Pro Phe Tyr Cys Gln Pro Cys Leu Asp Cys
    130                 135                 140

Gly Ala Leu His Arg His Thr Arg Leu Leu Cys Ser Arg Arg Asp Thr
145                 150                 155                 160

Asp Cys Gly Thr Cys Leu Pro Gly Phe Tyr Glu His Gly Asp Gly Cys
```

-continued

```
                165             170             175
Val Ser Cys Pro Thr Ser Thr Leu Gly Ser Cys Pro Glu Arg Cys Ala
            180                 185                 190
Ala Val Cys Gly Trp Arg Gln Met Phe Trp Val Gln Val Leu Leu Ala
            195                 200                 205
Gly Leu Val Val Pro Leu Leu Leu Gly Ala Thr Leu Thr Tyr Thr Tyr
            210                 215                 220
Arg His Cys Trp Pro His Lys Pro Leu Val Thr Ala Asp Glu Ala Gly
225                 230                 235                 240
Met Glu Ala Leu Thr Pro Pro Ala Thr His Leu Ser Pro Leu Asp
                245                 250                 255
Ser Ala His Thr Leu Leu Ala Pro Pro Asp Ser Ser Glu Lys Ile Cys
                260                 265                 270
Thr Val Gln Leu Val Gly Asn Ser Trp Thr Pro Gly Tyr Pro Glu Thr
                275                 280                 285
Gln Glu Ala Leu Cys Pro Gln Val Thr Trp Ser Trp Asp Gln Leu Pro
            290                 295                 300
Ser Arg Ala Leu Gly Pro Ala Ala Ala Pro Thr Leu Ser Pro Glu Ser
305                 310                 315                 320
Pro Ala Gly Ser Pro Ala Met Met Leu Gln Pro Gly Pro Gln Leu Tyr
                325                 330                 335
Asp Val Met Asp Ala Val Pro Ala Arg Arg Trp Lys Glu Phe Val Arg
                340                 345                 350
Thr Leu Gly Leu Arg Glu Ala Glu Ile Glu Ala Val Glu Val Glu Ile
                355                 360                 365
Gly Arg Phe Arg Asp Gln Gln Tyr Glu Met Leu Lys Arg Trp Arg Gln
            370                 375                 380
Gln Gln Pro Ala Gly Leu Gly Ala Val Tyr Ala Ala Leu Glu Arg Met
385                 390                 395                 400
Gly Leu Asp Gly Cys Val Glu Asp Leu Arg Ser Arg Leu Gln Arg Gly
                405                 410                 415
Pro (2) INFORMATION FOR SEQ ID NO:3:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (ii) MOLECULE TYPE: peptide (vii) IMMEDIATE SOURCE:
        (B) CLONE: FLAG_ peptide (xi) SEQUENCE DESCRIPTION: SEQ ID NO:3:

Asp Tyr Lys Asp Asp Asp Asp Lys
  1               5

(2) INFORMATION FOR SEQ ID NO:4:

(i) SEQUENCE CHARACTERISTICS:
        (A) LENGTH: 232 amino acids
        (B) TYPE: amino acid
        (C) STRANDEDNESS: Not Relevant
        (D) TOPOLOGY: linear (ii) MOLECULE TYPE: protein
```

(vi) ORIGINAL SOURCE:
    (A) ORGANISM: Human (vii) IMMEDIATE SOURCE:
    (B) CLONE: IgG1 Fc mutein (xi) SEQUENCE DESCRIPTION: SEQ ID NO:4:

```
Glu Pro Arg Ser Cys Asp Lys Thr His Thr Cys Pro Pro Cys Pro Ala
 1               5                  10                  15
Pro Glu Ala Glu Gly Ala Pro Ser Val Phe Leu Phe Pro Pro Lys Pro
            20                  25                  30
Lys Asp Thr Leu Met Ile Ser Arg Thr Pro Glu Val Thr Cys Val Val
        35                  40                  45
Val Asp Val Ser His Glu Asp Pro Glu Val Lys Phe Asn Trp Tyr Val
    50                  55                  60
Asp Gly Val Glu Val His Asn Ala Lys Thr Lys Pro Arg Glu Glu Gln
 65                  70                  75                  80
Tyr Asn Ser Thr Tyr Arg Val Val Ser Val Leu Thr Val Leu His Gln
                85                  90                  95
Asp Trp Leu Asn Gly Lys Asp Tyr Lys Cys Lys Val Ser Asn Lys Ala
            100                 105                 110
Leu Pro Ala Pro Met Gln Lys Thr Ile Ser Lys Ala Lys Gly Gln Pro
        115                 120                 125
Arg Glu Pro Gln Val Tyr Thr Leu Pro Pro Ser Arg Asp Glu Leu Thr
    130                 135                 140
Lys Asn Gln Val Ser Leu Thr Cys Leu Val Lys Gly Phe Tyr Pro Arg
145                 150                 155                 160
His Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Lys
225                 230
```

(2) INFORMATION FOR SEQ ID NO:5:

(i) SEQUENCE CHARACTERISTICS:
        (A) LENGTH: 1251 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Murine AIR (ix) FEATURE:
        (A) NAME/KEY: CDS
        (B) LOCATION: 7..1239

(xi) SEQUENCE DESCRIPTION: SEQ ID NO:5:

```
GTCGAC ATG GAG GCA CGG CTG CTG CGG GGC TGC GTG GTG GAG CCT CTG          48
       Met Glu Ala Arg Leu Leu Arg Gly Cys Val Val Glu Pro Leu
```

```
                1                5                    10
TTC CTA CCA CTG CTG CTG CTG CTG CTG CTG CTT GGT GGC CAG GGC              96
Phe Leu Pro Leu Leu Leu Leu Leu Leu Leu Leu Gly Gly Gln Gly
 15              20                  25                  30

CAG GGC GGC ATG TCT GGC AGG TGT GAC TGT GCC AGT GAG TCC CAG AAG        144
Gln Gly Gly Met Ser Gly Arg Cys Asp Cys Ala Ser Glu Ser Gln Lys
                 35                  40                  45

AGG TAT GGC CCG TTT TGT TGC AGG GGC TGC CCA AAG GGA CAC TAC ATG        192
Arg Tyr Gly Pro Phe Cys Cys Arg Gly Cys Pro Lys Gly His Tyr Met
             50                  55                  60

AAG GCC CCC TGC GCA GAA CCC TGT GGC AAC TCC ACC TGC CTT CCC TGT        240
Lys Ala Pro Cys Ala Glu Pro Cys Gly Asn Ser Thr Cys Leu Pro Cys
         65                  70                  75

CCC TCG GAC ACC TTC TTG ACC AGA GAC AAC CAC TTT AAG ACT GAC TGT        288
Pro Ser Asp Thr Phe Leu Thr Arg Asp Asn His Phe Lys Thr Asp Cys
     80                  85                  90

ACC CGC TGC CAA GTC TGT GAT GAA GAG GCC CTT CAA GTG ACC CTT GAG        336
Thr Arg Cys Gln Val Cys Asp Glu Glu Ala Leu Gln Val Thr Leu Glu
 95                 100                 105                 110

AAC TGC TCG GCA AAG TCG GAC ACC CAC TGT GGC TGC CAG TCA GGC TGG        384
Asn Cys Ser Ala Lys Ser Asp Thr His Cys Gly Cys Gln Ser Gly Trp
                115                 120                 125

TGT GTT GAC TGC TCC ACC GAG CCA TGT GGG AAA AGC TCA CCT TTC TCT        432
Cys Val Asp Cys Ser Thr Glu Pro Cys Gly Lys Ser Ser Pro Phe Ser
            130                 135                 140

TGT GTC CCA TGC GGG GCT ACA ACA CCA GTC CAT GAG GCT CCA ACC CCC        480
Cys Val Pro Cys Gly Ala Thr Thr Pro Val His Glu Ala Pro Thr Pro
        145                 150                 155

CGG CCC TGC CTG CCT GGC TTC TAT ATA CGT GGC AAT GAC TGC ACG TCC        528
Arg Pro Cys Leu Pro Gly Phe Tyr Ile Arg Gly Asn Asp Cys Thr Ser
    160                 165                 170

TGC CCC ACG GGC TTC AGC AGC GTT TGC CCT AAG GCT TGC ACT GCT GTC        576
Cys Pro Thr Gly Phe Ser Ser Val Cys Pro Lys Ala Cys Thr Ala Val
175                 180                 185                 190

TGT GGC TGG AAG CAG ATG TTT TGG GTC CAG GTG CTT CTA GGA GTC GCG        624
Cys Gly Trp Lys Gln Met Phe Trp Val Gln Val Leu Leu Gly Val Ala
                195                 200                 205

TTC CTT TTT GGG GCT ATC CTG ATC TGT GCA TAT TGT CGA TGG CAG CCT        672
Phe Leu Phe Gly Ala Ile Leu Ile Cys Ala Tyr Cys Arg Trp Gln Pro
            210                 215                 220

TGT AAG GCC GTG GTC ACT GCA GAC ACA GCT GGG ACG GAG ACC CTG GCC        720
Cys Lys Ala Val Val Thr Ala Asp Thr Ala Gly Thr Glu Thr Leu Ala
        225                 230                 235

TCA CCA CAG ACT GCC CAT CTC TCA GCC TCA GAC AGC GCC CAC ACC CTC        768
Ser Pro Gln Thr Ala His Leu Ser Ala Ser Asp Ser Ala His Thr Leu
    240                 245                 250

CTG GCA CCT CCA AGC AGT ACT GGG AAA ATC TGT ACC ACT GTC CAG TTG        816
Leu Ala Pro Pro Ser Ser Thr Gly Lys Ile Cys Thr Thr Val Gln Leu
255                 260                 265                 270

GTA GGC AAC AAC TGG ACC CCT GGC TTA TCC CAG ACT CAG GAG GTG GTC        864
Val Gly Asn Asn Trp Thr Pro Gly Leu Ser Gln Thr Gln Glu Val Val
                275                 280                 285

TGC GGA CAG GCC TCA CAA CCC TGG GAT CAG CTG CCA AAC AGA ACT CTT        912
Cys Gly Gln Ala Ser Gln Pro Trp Asp Gln Leu Pro Asn Arg Thr Leu
            290                 295                 300

GGA ACT CCT CTG GCA TCT CCG CTC TCG CCA GCG CCC CTG CGG GGC TCT        960
Gly Thr Pro Leu Ala Ser Pro Leu Ser Pro Ala Pro Leu Arg Gly Ser
        305                 310                 315

CCG GCT GCT GTG CTC CAG CCT GGC CCG CAG CTC TAC GAT GTG ATG GAT       1008
```

-continued

```
Pro Ala Ala Val Leu Gln Pro Gly Pro Gln Leu Tyr Asp Val Met Asp
            320                 325                 330

GCG GTC CCA GCA CGA AGG TGG AAG GAG TTC GTG CGC ACG CTG GGG CTG         1056
Ala Val Pro Ala Arg Arg Trp Lys Glu Phe Val Arg Thr Leu Gly Leu
335                 340                 345                 350

CGG GAA GCG GAA ATT GAA GCC GTG GAG GTG GAA ATC TGC CGC TTC CGA         1104
Arg Glu Ala Glu Ile Glu Ala Val Glu Val Glu Ile Cys Arg Phe Arg
                    355                 360                 365

GAC CAG CAG TAT GAG ATG CTC AAG CGC TGG CGT CAG CAG CAG CCT GCA         1152
Asp Gln Gln Tyr Glu Met Leu Lys Arg Trp Arg Gln Gln Gln Pro Ala
                370                 375                 380

GGC CTC GGT GCC ATC TAT GCG GCT CTG GAG CGC ATG GGT CTG GAA GGC         1200
Gly Leu Gly Ala Ile Tyr Ala Ala Leu Glu Arg Met Gly Leu Glu Gly
            385                 390                 395

TGT GCC GAG GAC CTG CGC AGC CGC CTG CAG CGT GGC CCG TGATGCGGCC         1249
Cys Ala Glu Asp Leu Arg Ser Arg Leu Gln Arg Gly Pro
        400                 405                 410

GC                                                                       1251
```

(2) INFORMATION FOR SEQ ID NO:6:

(i) SEQUENCE CHARACTERISTICS:
        (A) LENGTH: 411 amino acids
        (B) TYPE: amino acid
        (D) TOPOLOGY: linear (ii) MOLECULE TYPE: protein (xi) SEQUENCE DESCRIPTION: SEQ ID NO:6:

```
Met Glu Ala Arg Leu Leu Arg Gly Cys Val Val Glu Pro Leu Phe Leu
1               5                   10                  15

Pro Leu Leu Leu Leu Leu Leu Leu Gly Gly Gln Gly Gln Gly
            20                  25                  30

Gly Met Ser Gly Arg Cys Asp Cys Ala Ser Glu Ser Gln Lys Arg Tyr
        35                  40                  45

Gly Pro Phe Cys Cys Arg Gly Cys Pro Lys Gly His Tyr Met Lys Ala
    50                  55                  60

Pro Cys Ala Glu Pro Cys Gly Asn Ser Thr Cys Leu Pro Cys Pro Ser
65                  70                  75                  80

Asp Thr Phe Leu Thr Arg Asp Asn His Phe Lys Thr Asp Cys Thr Arg
                85                  90                  95

Cys Gln Val Cys Asp Glu Glu Ala Leu Gln Val Thr Leu Glu Asn Cys
            100                 105                 110

Ser Ala Lys Ser Asp Thr His Cys Gly Cys Gln Ser Gly Trp Cys Val
        115                 120                 125

Asp Cys Ser Thr Glu Pro Cys Gly Lys Ser Ser Pro Phe Ser Cys Val
    130                 135                 140

Pro Cys Gly Ala Thr Thr Pro Val His Glu Ala Pro Thr Pro Arg Pro
145                 150                 155                 160

Cys Leu Pro Gly Phe Tyr Ile Arg Gly Asn Asp Cys Thr Ser Cys Pro
                165                 170                 175

Thr Gly Phe Ser Ser Val Cys Pro Lys Ala Cys Thr Ala Val Cys Gly
            180                 185                 190

Trp Lys Gln Met Phe Trp Val Gln Val Leu Leu Gly Val Ala Phe Leu
        195                 200                 205

Phe Gly Ala Ile Leu Ile Cys Ala Tyr Cys Arg Trp Gln Pro Cys Lys
    210                 215                 220
```

-continued

```
Ala Val Val Thr Ala Asp Thr Ala Gly Thr Glu Thr Leu Ala Ser Pro
225                 230             235                 240

Gln Thr Ala His Leu Ser Ala Ser Asp Ser Ala His Thr Leu Leu Ala
            245                 250             255

Pro Pro Ser Ser Thr Gly Lys Ile Cys Thr Thr Val Gln Leu Val Gly
            260             265             270

Asn Asn Trp Thr Pro Gly Leu Ser Gln Thr Gln Glu Val Val Cys Gly
        275                 280             285

Gln Ala Ser Gln Pro Trp Asp Gln Leu Pro Asn Arg Thr Leu Gly Thr
        290             295             300

Pro Leu Ala Ser Pro Leu Ser Pro Ala Pro Pro Ala Gly Ser Pro Ala
305             310             315                 320

Ala Val Leu Gln Pro Gly Pro Gln Leu Tyr Asp Val Met Asp Ala Val
            325             330             335

Pro Ala Arg Arg Trp Lys Glu Phe Val Arg Thr Leu Gly Leu Arg Glu
            340             345             350

Ala Glu Ile Glu Ala Val Glu Val Glu Ile Cys Arg Phe Arg Asp Gln
        355             360             365

Gln Tyr Glu Met Leu Lys Arg Trp Arg Gln Gln Pro Ala Gly Leu
    370             375             380

Gly Ala Ile Tyr Ala Ala Leu Glu Arg Met Gly Leu Glu Gly Cys Ala
385             390             395                 400

Glu Asp Leu Arg Ser Arg Leu Gln Arg Gly Pro
            405             410
```